(12) United States Patent
Finn et al.

(10) Patent No.: US 11,079,285 B2
(45) Date of Patent: Aug. 3, 2021

(54) AUTOMATED ANALYSIS OF THERMALLY-SENSITIVE COATING AND METHOD THEREFOR

(71) Applicant: United Technologies Corporation, Farmington, CT (US)

(72) Inventors: Alan Matthew Finn, Hebron, CT (US); Serge L. Shishkin, Marlborough, CT (US); Ziyou Xiong, Wethersfield, CT (US); Thomas J. Martin, East Hampton, CT (US); Scott A. Liljenberg, Wethersfield, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 614 days.

(21) Appl. No.: 15/971,277

(22) Filed: May 4, 2018

(65) Prior Publication Data

US 2019/0339131 A1 Nov. 7, 2019

(51) Int. Cl.
| | |
|---|---|
| *G01K 1/00* | (2006.01) |
| *G01J 5/60* | (2006.01) |
| *G01J 3/46* | (2006.01) |
| *G01K 11/12* | (2021.01) |
| *G01N 25/18* | (2006.01) |
| *G01J 5/00* | (2006.01) |

(52) U.S. Cl.
CPC ............... *G01J 5/60* (2013.01); *G01J 3/462* (2013.01); *G01K 11/12* (2013.01); *G01J 2005/0077* (2013.01); *G01N 25/18* (2013.01)

(58) Field of Classification Search
CPC ......... G06F 17/5009; G01J 5/60; G01J 3/462; G01K 11/12

USPC ........................................................ 702/130
See application file for complete search history.

(56) References Cited

U.S. PATENT DOCUMENTS

| | | |
|---|---|---|
| 3,804,397 A | 4/1974 | Neumann |
| 4,402,053 A | 8/1983 | Kelley et al. |
| 4,403,294 A | 9/1983 | Hamada et al. |
| 4,873,651 A | 10/1989 | Raviv |
| 5,064,291 A | 11/1991 | Reiser |

(Continued)

FOREIGN PATENT DOCUMENTS

| | | |
|---|---|---|
| CA | 2820732 A1 | 12/2014 |
| DE | 19710743 A1 | 9/1998 |

(Continued)

OTHER PUBLICATIONS

Gao et al., 'A Statistical Method for Crack Detection from Vibrothermography Inspection Data',(2010) Statistics Preprints. Paper 68. http://lib.dr.iastate.edu/stat_las_preprints/68.

(Continued)

*Primary Examiner* — Aditya S Bhat
(74) *Attorney, Agent, or Firm* — Bachman & LaPointe, P.C.

(57) ABSTRACT

A method for thermally-sensitive coating analysis of a component includes imaging the coated, exposed component over a range of distinct frequencies as selected by a narrowband variable filter; estimating parameters of non-uniformity correction (NUC) for every pixel at every wavelength; constructing a 2D temperature map on a pixel-by-pixel basis using the non-uniformity correction; and mapping the 2D temperature map to a 3D computer aided design (CAD) model.

20 Claims, 7 Drawing Sheets

(56) References Cited

U.S. PATENT DOCUMENTS

| | | |
|---|---|---|
| 5,119,678 A | 6/1992 | Bashyam et al. |
| 5,345,514 A | 9/1994 | Mandavieh et al. |
| 5,345,515 A | 9/1994 | Nishi et al. |
| 5,351,078 A | 9/1994 | Lemelson |
| 5,963,328 A | 10/1999 | Yoshida et al. |
| 6,023,637 A | 2/2000 | Liu et al. |
| 6,153,889 A | 11/2000 | Jones |
| 6,177,682 B1 | 1/2001 | Bartulovic et al. |
| 6,271,520 B1 | 8/2001 | Tao et al. |
| 6,399,948 B1 | 6/2002 | Thomas |
| 6,434,267 B1 | 8/2002 | Smith |
| 6,462,813 B1 | 10/2002 | Haven et al. |
| 6,690,016 B1 | 2/2004 | Watkins et al. |
| 6,737,648 B2 | 5/2004 | Fedder et al. |
| 6,759,659 B2 | 7/2004 | Thomas et al. |
| 6,804,622 B2 | 10/2004 | Bunker et al. |
| 6,907,358 B2 | 6/2005 | Suh et al. |
| 6,965,120 B1 | 11/2005 | Beyerer et al. |
| 7,026,811 B2 | 4/2006 | Roney, Jr. et al. |
| 7,064,330 B2 | 6/2006 | Raulerson et al. |
| 7,119,338 B2 | 10/2006 | Thompson et al. |
| 7,122,801 B2 | 10/2006 | Favro et al. |
| 7,129,492 B2 | 10/2006 | Saito et al. |
| 7,164,146 B2 | 1/2007 | Weir et al. |
| 7,190,162 B2 | 3/2007 | Tenley et al. |
| 7,220,966 B2 | 5/2007 | Saito et al. |
| 7,233,867 B2 | 6/2007 | Pisupati et al. |
| 7,240,556 B2 | 7/2007 | Georgeson et al. |
| 7,272,529 B2 | 9/2007 | Hogan et al. |
| 7,313,961 B2 | 1/2008 | Tenley et al. |
| 7,415,882 B2 | 8/2008 | Fetzer et al. |
| 7,446,886 B2 | 11/2008 | Aufmuth et al. |
| 7,489,811 B2 | 2/2009 | Brummel et al. |
| 7,602,963 B2 | 10/2009 | Nightingale et al. |
| 7,689,030 B2 | 3/2010 | Suh et al. |
| 7,724,925 B2 | 5/2010 | Shepard |
| 7,738,725 B2 | 6/2010 | Raskar et al. |
| 7,823,451 B2 | 11/2010 | Sarr |
| 7,966,883 B2 | 6/2011 | Lorraine et al. |
| 8,050,491 B2 | 11/2011 | Vaidyanathan |
| 8,204,294 B2 | 6/2012 | Alloo et al. |
| 8,208,711 B2 | 6/2012 | Venkatachalam et al. |
| 8,221,825 B2 | 7/2012 | Reitz et al. |
| 8,239,424 B2 | 8/2012 | Haigh et al. |
| 8,413,917 B2 | 4/2013 | Wang et al. |
| 8,449,176 B2 | 5/2013 | Shepard |
| 8,520,931 B2 | 8/2013 | Tateno |
| 8,528,317 B2 | 9/2013 | Gerez et al. |
| 8,692,887 B2 | 4/2014 | Ringermacher et al. |
| 8,744,166 B2 | 6/2014 | Scheid et al. |
| 8,761,490 B2 | 6/2014 | Scheid et al. |
| 8,781,209 B2 | 7/2014 | Scheid et al. |
| 8,781,210 B2 | 7/2014 | Scheid et al. |
| 8,792,705 B2 | 7/2014 | Scheid et al. |
| 8,913,825 B2 | 12/2014 | Taguchi et al. |
| 8,983,794 B1 | 3/2015 | Motzer et al. |
| 9,037,381 B2 | 5/2015 | Care |
| 9,046,497 B2 | 6/2015 | Kush et al. |
| 9,066,028 B1 | 6/2015 | Koshti |
| 9,080,453 B2 | 7/2015 | Shepard et al. |
| 9,116,071 B2 | 8/2015 | Hatcher, Jr. et al. |
| 9,134,280 B2 | 9/2015 | Cataldo et al. |
| 9,146,205 B2 | 9/2015 | Renshaw et al. |
| 9,151,698 B2 | 10/2015 | Jahnke et al. |
| 9,154,743 B2 | 10/2015 | Hatcher, Jr. et al. |
| 9,240,049 B2 | 1/2016 | Ciurea et al. |
| 9,251,582 B2 | 2/2016 | Lim et al. |
| 9,300,865 B2 | 3/2016 | Wang et al. |
| 9,305,345 B2 | 4/2016 | Lim et al. |
| 9,458,735 B1 | 10/2016 | Diwinsky et al. |
| 9,465,385 B2 | 10/2016 | Kamioka et al. |
| 9,467,628 B2 | 10/2016 | Geng et al. |
| 9,471,057 B2 | 10/2016 | Scheid et al. |
| 9,476,798 B2 | 10/2016 | Pandey et al. |
| 9,476,842 B2 | 10/2016 | Drescher et al. |
| 9,483,820 B2 | 11/2016 | Lim et al. |
| 9,488,592 B1 | 11/2016 | Maresca et al. |
| 9,519,844 B1 | 12/2016 | Thompson et al. |
| 9,594,059 B1 | 3/2017 | Brady et al. |
| 9,734,568 B2 | 5/2017 | Vajaria et al. |
| 9,785,919 B2 | 10/2017 | Diwinsky et al. |
| 9,804,997 B2 | 10/2017 | Sharp et al. |
| 9,808,933 B2 | 11/2017 | Lin et al. |
| 9,981,382 B1 | 5/2018 | Strauss et al. |
| 10,438,036 B1 | 10/2019 | Reome et al. |
| 2002/0121602 A1 | 9/2002 | Thomas et al. |
| 2002/0167660 A1 | 11/2002 | Zaslavsky |
| 2003/0117395 A1 | 6/2003 | Yoon |
| 2003/0205671 A1 | 11/2003 | Thomas et al. |
| 2004/0089811 A1 | 5/2004 | Lewis et al. |
| 2004/0089812 A1 | 5/2004 | Favro et al. |
| 2004/0139805 A1 | 7/2004 | Antonelli et al. |
| 2004/0201672 A1 | 10/2004 | Varadarajan et al. |
| 2004/0240600 A1 | 12/2004 | Freyer et al. |
| 2004/0245469 A1 | 12/2004 | Favro et al. |
| 2004/0247170 A1 | 12/2004 | Furze et al. |
| 2005/0008215 A1 | 1/2005 | Shepard |
| 2005/0113060 A1 | 5/2005 | Lowery |
| 2005/0151083 A1 | 7/2005 | Favro et al. |
| 2005/0167596 A1 | 8/2005 | Rothenfusser et al. |
| 2005/0276907 A1 | 12/2005 | Harris et al. |
| 2006/0012790 A1 | 1/2006 | Furze et al. |
| 2006/0078193 A1 | 4/2006 | Brummel et al. |
| 2006/0086912 A1 | 4/2006 | Weir et al. |
| 2007/0007733 A1 | 1/2007 | Hogarth et al. |
| 2007/0017297 A1 | 1/2007 | Georgeson et al. |
| 2007/0045544 A1 | 3/2007 | Favro et al. |
| 2008/0022775 A1 | 1/2008 | Sathish et al. |
| 2008/0053234 A1 | 3/2008 | Staroselsky et al. |
| 2008/0075484 A1* | 3/2008 | Komiya ............... G03G 15/556 399/39 |
| 2008/0111074 A1 | 5/2008 | Weir et al. |
| 2008/0183402 A1 | 7/2008 | Malkin et al. |
| 2008/0229834 A1 | 9/2008 | Bossi et al. |
| 2008/0247635 A1 | 10/2008 | Davis et al. |
| 2008/0247636 A1 | 10/2008 | Davis et al. |
| 2009/0000382 A1 | 1/2009 | Sathish et al. |
| 2009/0010507 A1 | 1/2009 | Geng |
| 2009/0066939 A1 | 3/2009 | Venkatachalam et al. |
| 2009/0128643 A1 | 5/2009 | Kondo et al. |
| 2009/0252987 A1 | 10/2009 | Greene, Jr. |
| 2009/0279772 A1 | 11/2009 | Sun et al. |
| 2009/0312956 A1 | 12/2009 | Zombo et al. |
| 2010/0124369 A1* | 5/2010 | Wu ......................... G01B 11/02 382/141 |
| 2010/0212430 A1 | 8/2010 | Murai et al. |
| 2010/0220910 A1 | 9/2010 | Kaucic et al. |
| 2011/0062339 A1 | 3/2011 | Ruhge et al. |
| 2011/0083705 A1 | 4/2011 | Stone et al. |
| 2011/0119020 A1 | 5/2011 | Key |
| 2011/0123093 A1 | 5/2011 | Alloo et al. |
| 2011/0299752 A1 | 12/2011 | Sun |
| 2011/0302694 A1 | 12/2011 | Wang et al. |
| 2012/0154599 A1 | 6/2012 | Huang |
| 2012/0188380 A1 | 7/2012 | Drescher et al. |
| 2012/0249959 A1 | 10/2012 | You et al. |
| 2012/0275667 A1 | 11/2012 | Lu |
| 2012/0293647 A1* | 11/2012 | Singh ..................... G06T 7/001 348/82 |
| 2013/0028478 A1 | 1/2013 | St-Pierre et al. |
| 2013/0041614 A1 | 2/2013 | Shepard et al. |
| 2013/0070897 A1 | 3/2013 | Jacotin |
| 2013/0113914 A1 | 5/2013 | Scheid et al. |
| 2013/0113916 A1 | 5/2013 | Scheid et al. |
| 2013/0163849 A1 | 6/2013 | Jahnke et al. |
| 2013/0235897 A1 | 9/2013 | Bouteyre et al. |
| 2013/0250067 A1 | 9/2013 | Laxhuber et al. |
| 2014/0022357 A1 | 1/2014 | Yu et al. |
| 2014/0056507 A1 | 2/2014 | Doyle et al. |
| 2014/0098836 A1 | 4/2014 | Bird |
| 2014/0184786 A1 | 7/2014 | Georgeson et al. |
| 2014/0185912 A1 | 7/2014 | Lim et al. |
| 2014/0198185 A1 | 7/2014 | Haugen et al. |
| 2014/0200832 A1 | 7/2014 | Troy et al. |

(56) References Cited

U.S. PATENT DOCUMENTS

| | | | |
|---|---|---|---|
| 2014/0350338 | A1 | 11/2014 | Tanaka et al. |
| 2015/0041654 | A1 | 2/2015 | Barychev et al. |
| 2015/0046098 | A1 | 2/2015 | Jack et al. |
| 2015/0086083 | A1 | 3/2015 | Chaudhry et al. |
| 2015/0128709 | A1 | 5/2015 | Stewart et al. |
| 2015/0138342 | A1 | 5/2015 | Brdar et al. |
| 2015/0185128 | A1 | 7/2015 | Chang et al. |
| 2015/0233714 | A1 | 8/2015 | Kim |
| 2015/0253266 | A1 | 9/2015 | Lucon et al. |
| 2015/0314901 | A1 | 11/2015 | Murray et al. |
| 2015/0371431 | A1* | 12/2015 | Korb .................. G06K 9/00208 382/113 |
| 2016/0012588 | A1 | 1/2016 | Taguchi et al. |
| 2016/0043008 | A1 | 2/2016 | Murray et al. |
| 2016/0109283 | A1 | 4/2016 | Broussais-Colella et al. |
| 2016/0178532 | A1 | 6/2016 | Lim et al. |
| 2016/0241793 | A1 | 8/2016 | Ravirala et al. |
| 2016/0284098 | A1 | 9/2016 | Okumura et al. |
| 2016/0314571 | A1 | 10/2016 | Finn et al. |
| 2016/0328835 | A1 | 11/2016 | Maresca, Jr. et al. |
| 2016/0334284 | A1 | 11/2016 | Kaplun Mucharrafille et al. |
| 2017/0011503 | A1 | 1/2017 | Newman |
| 2017/0023505 | A1 | 1/2017 | Maione et al. |
| 2017/0052152 | A1 | 2/2017 | Tat et al. |
| 2017/0085760 | A1 | 3/2017 | Ernst et al. |
| 2017/0090458 | A1 | 3/2017 | Lim et al. |
| 2017/0122123 | A1 | 5/2017 | Kell et al. |
| 2017/0142302 | A1 | 5/2017 | Shaw et al. |
| 2017/0184469 | A1 | 6/2017 | Chang et al. |
| 2017/0184549 | A1 | 6/2017 | Reed et al. |
| 2017/0184650 | A1 | 6/2017 | Chang et al. |
| 2017/0211408 | A1 | 7/2017 | Ahmadian et al. |
| 2017/0219815 | A1 | 8/2017 | Letter et al. |
| 2017/0221274 | A1 | 8/2017 | Chen et al. |
| 2017/0234837 | A1 | 8/2017 | Hall et al. |
| 2017/0241286 | A1 | 8/2017 | Roberts et al. |
| 2017/0258391 | A1 | 9/2017 | Finn et al. |
| 2017/0262965 | A1 | 9/2017 | Xiong et al. |
| 2017/0262977 | A1 | 9/2017 | Finn et al. |
| 2017/0262979 | A1 | 9/2017 | Xiong et al. |
| 2017/0262985 | A1 | 9/2017 | Finn et al. |
| 2017/0262986 | A1 | 9/2017 | Xiong et al. |
| 2017/0270651 | A1 | 9/2017 | Bailey et al. |
| 2017/0284971 | A1 | 10/2017 | Hall |
| 2017/0297095 | A1 | 10/2017 | Zalameda et al. |
| 2018/0002039 | A1 | 1/2018 | Finn et al. |
| 2018/0005362 | A1 | 1/2018 | Wang et al. |
| 2018/0013959 | A1 | 1/2018 | Slavens et al. |
| 2018/0019097 | A1 | 1/2018 | Harada et al. |
| 2018/0098000 | A1 | 4/2018 | Park et al. |
| 2018/0111239 | A1 | 4/2018 | Zak et al. |
| 2019/0299542 | A1 | 10/2019 | Webb |
| 2019/0338666 | A1 | 11/2019 | Finn et al. |
| 2019/0339165 | A1 | 11/2019 | Finn et al. |
| 2019/0339206 | A1 | 11/2019 | Xiong et al. |
| 2019/0339207 | A1 | 11/2019 | Finn et al. |
| 2019/0339234 | A1 | 11/2019 | Finn et al. |
| 2019/0339235 | A1 | 11/2019 | Finn et al. |
| 2019/0340721 | A1 | 11/2019 | Finn et al. |
| 2019/0340742 | A1 | 11/2019 | Finn et al. |
| 2019/0340805 | A1 | 11/2019 | Xiong et al. |
| 2019/0342499 | A1 | 11/2019 | Xiong et al. |

FOREIGN PATENT DOCUMENTS

| | | |
|---|---|---|
| EP | 1961919 A2 | 8/2008 |
| GB | 2545271 A | 6/2017 |
| JP | 06235700 A | 8/1994 |
| JP | 2015161247 A | 9/2015 |
| SG | 191452 A1 | 7/2013 |
| WO | 2013088709 A1 | 6/2013 |
| WO | 2016112018 A1 | 7/2016 |
| WO | 2016123508 A1 | 8/2016 |
| WO | 2016176524 A1 | 11/2016 |

OTHER PUBLICATIONS

Li1 Ming; Holland1 Stephen D.; and Meeker1 William Q.1 "Statistical Methods for Automatic Crack Detection Based on Vibrothermography Sequence-of-Images Data" (2010). Statistics Preprints. 69.

Henneke et al. 'Detection of Damage in Composite Materials by Vibrothermography', ASTM special technical publication (696), American Society for Testing and Materials, 1979, pp. 83-95.

http://www.npl.co.uk/commercial-services/sector-case-studies/thermal-imaging-reveals-the-invisible; Apr. 17, 2012.

Tian et al., 'A Statistical Framework for Improved Automatic Flaw Detection in Nondestructive Evaluation Images', Technometrics, 59, 247-261. Feb. 1, 2017.

Emmanuel J. Cand'es1,2, Xiaodong Li2, Yi Ma3,4, and John Wright4, "Robust Principal Component Analysis", (1)Department of Statistics, Stanford University, Stanford, CA; (2)Department of Mathematics, Stanford University, Stanford, CA; (3,4) Electrical and Computer Engineering, UIUC, Urbana, IL (4) Microsoft Research Asia, Beijing, China, Dec. 17, 2009.

Sebastien Parent; "From Human to Machine: How to Be Prepared for Integration of Automated Visual Inspection" Quality Magazine, https://www.qualitymag.com/articles/91976. Jul. 2, 2014.

http://www.yxlon.com/products/x-ray-and-ct-inspection-systems/yxlon-mu56-tb, 2016.

U.S. Office action dated Jul. 23, 2018 issued in corresponding U.S. Appl. No. 15/971,254.

U.S. Non-Final Office Action dated Apr. 30, 2020 issued for corresponding U.S. Appl. No. 15/970,944.

U.S. Non-Final Office Action dated Mar. 5, 2019 for corresponding U.S. Appl. No. 15/971,227.

U.S. Final Office Action dated Jan. 3, 2019 for corresponding U.S. Appl. No. 15/971,254.

U.S. Final Office Action dated Mar. 12, 2020 for corresponding U.S. Appl. No. 15/971,194.

U.S. Non-Final Office Action dated Feb. 25, 2020 for corresponding U.S. Appl. No. 15/971,214.

U.S. Non-Final Office Action dated May 28, 2019 for corresponding U.S. Appl. No. 15/971,214.

U.S. Non-Final Office Action dated Nov. 26, 2019 for corresponding U.S. Appl. No. 15/971,194.

U.S. Non-Final Office Action dated Apr. 16, 2019 for corresponding U.S. Appl. No. 15/970,985.

Blachnio et al, "Assessment of Technical Condition Demonstrated by Gas Turbine Blades by Processing of Images of Their Surfaces", Journal of KONBiN, 1(21), 2012, pp. 41-50.

Raskar et al., 'A Non-photorealistic Camera: Depth Edge Detection and Stylized Rendering using Multi-flash Imaging' ACM Transactions on Graphics, 2004 http://www.merl.com/publications/docs/TR2006-107.pdf.

Feris et al., 'Specular Reflection Reduction with Multi-Flash Imaging', 17th Brazilian Symposium on Computer Graphics and Image Processing, 2004. http://rogerioferis.com/publications/FerisSIB04.pdf.

Holland, "First Measurements from a New Broadband Vibrothermography Measurement System", AIP Conference Proceedings, 894 (2007), pp. 478-483. http://link.aip.org/link/doi/10.1063/1.2718010 \.

Gao et al., 'Detecting Cracks in Aircraft Engine Fan Blades Using Vibrothermography Nondestructive Evaluation', RESS Special Issue on Accelerated Testing, 2014, http://dx.doi.org/10.1016/j.ress.2014.05.009.

Gao et al., 'A Statistical Method for Crack Detection from Vibrothermography Inspection Data', Statistics Preprints. Paper 68. http://lib.dr.iastate.edu/stat_las_preprints/68.

Holland, 'Thermographic Signal Reconstruction for Vibrothermography', Infrared Physics & Technology 54 (2011) 503-511.

Li et al., 'Statistical Methods for Automatic Crack Detection Based on Vibrothermography Sequence-of-Images Data', Statistics Preprints. Paper 69. http://lib.dr.iastate.edu/stat_las_preprints/69.

(56) References Cited

OTHER PUBLICATIONS

Tian et al., 'A Statistical Framework for Improved Automatic Flaw Detection in Nondestructive Evaluation Images', Technometrics, 59, 247-261.

Henneke et al. 'Detection of Damage in Composite Materials by Vibrothermography', ASTM special technical publication (696), 1979, pp. 83-95.

http://www.npl.co.uk/commercial-services/sector-case-studies/thermal-imaging-reveals-the-invisible.

U.S. Notice of Allowance dated Oct. 19, 2020 issued for corresponding U.S. Appl. No. 15/971,270.

U.S. Non-Final Office Action dated Nov. 29, 2019 for corresponding U.S. Appl. No. 15/971,242.

E. J. Candès, X. Li, Y. Ma, and J. Wright, "Robust Principal Component Analysis", submitted. http://www-stat.stanford.edu/~candes/papers/RobustPCA.pdf.

M. Sznaier, O. Camps, N. Ozay, T. Ding, G. Tadmor and D. Brooks, "The Role of Dynamics in Extracting Information Sparsely Encoded in High Dimensional Data Streams", in Dynamics of Information Systems, Hirsch, M.J.; Pardalos, P.M.; Murphey, R. (Eds.), pp. 1-28, Springer Verlag, 2010.

M. Fazel, H. Hindi, and S. Boyd, "A Rank Minimization Heuristic with Application to Minimum Order System Approximation", American Control Conference, Arlington, Virginia, pp. 4734-4739, Jun. 2001.

Meola et al., 'An Excursus on Infrared Thermography Imaging', J. Imaging 2016, 2, 36 http://www.mdpi.com/2313-433X/2/4/36/pdf.

Yu et al., 'ASIFT: An Algorithm for Fully Affine Invariant Comparison', Image Processing on Line on Feb. 24, 2011. http://www.ipol.im/pub/art/2011/my-asift/article.pdf.

Schemmel et al., 'Measurement of Direct Strain Optic Coefficient of YSZ Thermal Barrier Coatings at Ghz Frequencies', Optics Express, v.25, n. 17, Aug. 21, 2017, https://doi.org/10.1364/OE.25.019968.

Jean-Yves Bouguet, "Camera Calibration Toolbox for Matlab", http://www.vision.caltech.edu/bouguetj/calib_doc/, accessed on Nov. 10, 2017.

https://www.qualitymag.com/articles/91976-from-human-to-machine-how-to-be-prepared-for-integration-of-automated-visual-inspection.

hittp://www.yxlon.com/products/x-ray-and-ct-inspection-systems/yxlon-mu56-tb.

Yu et al. 'Shadow Graphs and 3D Texture Reconstruction', IJCV, vol. 62, No. 1-2, 2005, pp. 35-60.

U.S. Final Office Action dated Jul. 28, 2020 issued for corresponding U.S. Appl. No. 15/971,214.

U.S. Final Office Action dated Aug. 27, 2020 issued for corresponding U.S. Appl. No. 15/970,944.

U.S. Non-Final Office Action dated Aug. 28, 2020 issued for corresponding U.S. Appl. No. 15/971,194.

U.S. Non-Final Office Action dated Jun. 23, 2020 issued for corresponding U.S. Appl. No. 15/971,205.

U.S. Non-Final Office Action dated May 21, 2020 issued for corresponding U.S. Appl. No. 15/971,236.

\* cited by examiner

AUTOMATED ANALYSIS OF THERMALLY-SENSITIVE COATING AND METHOD THEREFOR

BACKGROUND

The present disclosure relates to nondestructive component inspection and, more particularly, to automated analysis of thermally-sensitive coating.

Mechanical components, especially for gas turbines, may be exposed to high temperatures during design or during operation. These components may be coated with a thermally-sensitive coating to indicate maximum temperature exposure, integrated time-temperature exposure, and the like. In some cases, the thermally-sensitive coating permanently changes color (an oxidation reaction) depending on duration and exposure temperature. Interpretation of the color change is often performed manually which may be tedious, time consuming, imprecise, and error prone.

SUMMARY

A method for thermally-sensitive coating analysis of a component, the method according to one disclosed non-limiting embodiment of the present disclosure includes performing one or more scans of a thermally-sensitive coated and thermally exposed component to generate image data; estimating parameters of non-uniformity correction (NUC) for one or more pixels of one or more dark field images and one or more corresponding pixels of one or more bright field images; constructing a 2D temperature map for one or more pixels of the scanned image using the parameters from the non-uniformity correction; and mapping the 2D temperature map to a 3D computer aided design (CAD) model.

A further aspect of the present disclosure includes scanning over one or more of a range of distinct frequencies as selected by a narrowband variable filter, a distinct range of polarizations, and a distinct range of incident angles.

A further aspect of the present disclosure includes defining a cost function and minimizing the error between the 3D coordinates by back-projecting features from the 2D temperature map.

A further aspect of the present disclosure includes using a non-linear least squares method.

A further aspect of the present disclosure includes defining intensities of one or more pixels of a dark field as null and defining intensities of corresponding one or more pixels of a bright field to a nominal intensity.

A further aspect of the present disclosure includes detecting bad pixels.

A further aspect of the present disclosure includes determining if a value or difference from a dark value to a bright value (slope) is greater than a threshold.

A further aspect of the present disclosure includes determining if a ratio from a bright value to a dark value (slope) is greater than a threshold.

A further aspect of the present disclosure includes that one or more of the scans, dark field images, and bright field images are filtered by one or more of a mean filter (averaging), a median filter, a rank filter, an adaptive filter, a low-pass filter, and inpainting.

A further aspect of the present disclosure includes that a dark value threshold is derived as being the mean+3σ of all the dark field values.

A further aspect of the present disclosure includes that a bright value threshold is derived as being the mean−3σ of all the bright field values.

A further aspect of the present disclosure includes that one or more of a dark value threshold is derived as being the mean+3σ of all the filtered dark field values, and a bright value threshold is derived as being the mean−3σ of all the filtered bright field values.

A further aspect of the present disclosure includes that one or more of a number of scans, number of dark field images, and number of bright field images is determined by the convergence of estimates for the mean, and a standard deviation as the number of scans increases.

A further aspect of the present disclosure includes that the estimates converge when additional scans change the estimate by less than a pre-defined amount.

A further aspect of the present disclosure includes that the pre-defined amount is 1%.

A further aspect of the present disclosure includes finding a correspondence between a feature of the 2D temperature map and a feature of the 3D model; recovering extrinsic parameters via optimization using the correspondence; transforming the 2D temperature map to derive positioning and orientation; and projecting the 2D temperature map with respect to the extrinsic parameters.

A thermally-sensitive coating analysis system according to one disclosed non-limiting embodiment of the present disclosure includes one or more of a narrowband multispectral filter, a polarization filter, an incident angle variation for the multispectral camera; and a control system operable to map a 2D temperature map from the multispectral camera to a 3D CAD model using image analytics in which repeated scans by the multispectral camera are filtered by the narrowband multispectral filter.

A further aspect of the present disclosure includes one or more repeated scans of a dark field image, a bright field image, a test coupon, and the component.

A further aspect of the present disclosure includes that the filtering comprises one or more of a mean filter (averaging), a median filter, a rank filter, an adaptive filter, a low-pass filter, and inpainting.

The foregoing features and elements may be combined in various combinations without exclusivity, unless expressly indicated otherwise. These features and elements as well as the operation thereof will become more apparent in light of the following description and the accompanying drawings. It should be understood; however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
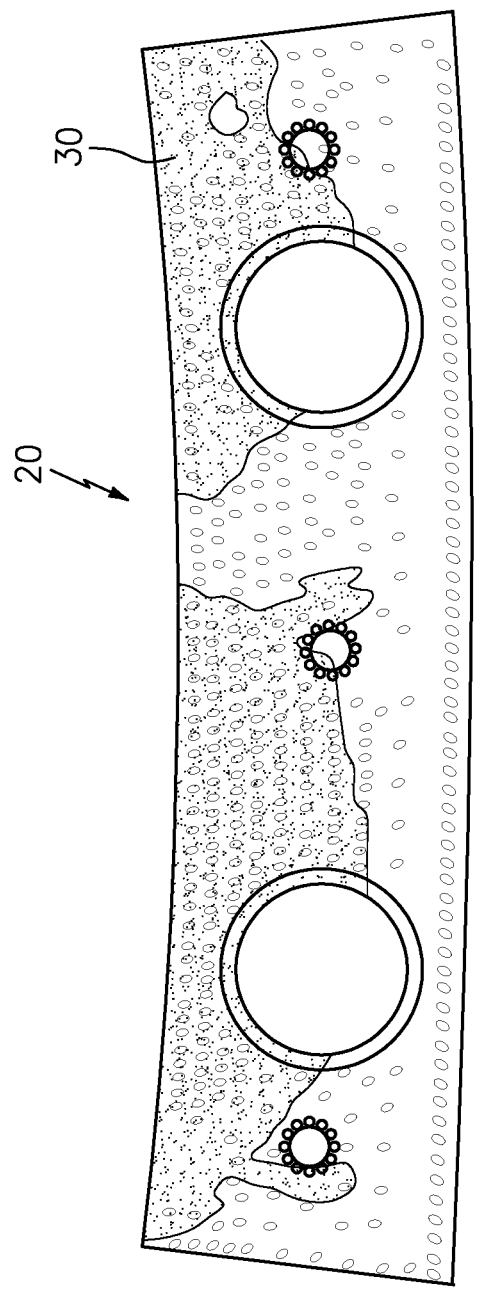
FIG. 1 is a schematic of an example gas turbine engine component that has been painted by a thermally-sensitive coating after exposure to a high temperature.

FIG. 1 schematically illustrates a component 20, such as a gas turbine engine component, that has been coated with a thermally-sensitive coating 30 and heated to create a color-temperature reference. Although a particular component is illustrated in the disclosed embodiment, it should be appreciated that various components will benefit herefrom. The thermally-sensitive coating 30 indicates maximum temperature exposure, integrated time-temperature exposure, and other temperature information. The thermally-sensitive coating 30 may permanently change color (an oxidation reaction) depending on the duration and temperature to which it is exposed. Different chemical compositions of thermally-sensitive coating 30 are relatively more or less sensitive and exhibit color changes over different color ranges (light frequencies) for different exposure temperatures and durations. The thermally-sensitive coating 30 may include many different thermally sensitive paints, e.g., part number MC520-7 by TMC Hallcrest, Inc.

Figure 2:
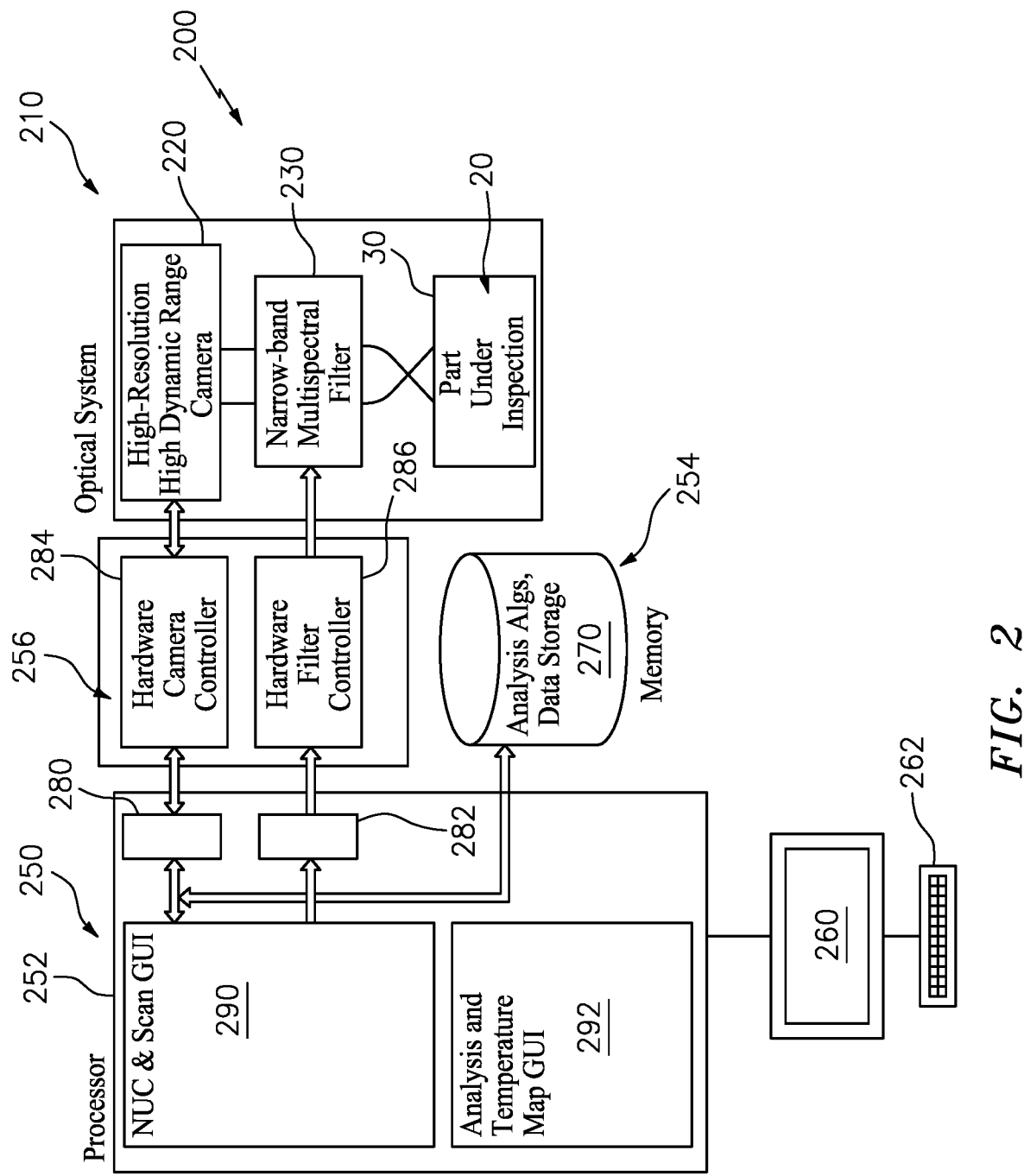
FIG. 2 is a schematic view of a nondestructive thermally-sensitive coating analysis system.

With reference to FIG. 2, a nondestructive thermally-sensitive coating analysis system 200 includes an optical system 210 with a high resolution, high dynamic range multispectral camera 220, a narrowband multispectral filter 230, and a control system 250. A prior art analysis system 200 may be an ISPEC 30-band multispectral camera from Geospatial Systems Inc., part number PM-UM-2005.1.00. covering a 400 nm-700 nm wavelength range that includes a relatively low resolution, low dynamic range commercial camera. Various commercial cameras such as the ISPEC camera can be further modified with additional lenses such as, for, example custom lenses with as small chromatic and geometrical distortions as possible. The ISPEC commercial camera may be beneficially replaced with a high-resolution, high-dynamic range camera. An example narrowband multispectral filter 230 as used in the PM-UM-2005.1.00 is an electro-optic Liquid Crystal Tunable Filter (LCTF) that operates as a programmable filter wheel. The LCTF has a fixed 10 nm bandpass and the center wavelength can be tuned in 10 nm increments across 400 nm-700 nm. The PM-UM-2005.1.00 control system tunes the LCTF through a range of wavelengths, takes a single exposure for a predefined exposure time and fixed aperture for each wavelength, and records the resulting image data set. Alternatively, control system 250 allows computer-controlled multiple exposures where the number of exposures is based on achieving a desired accuracy as explained elsewhere herein. This may include computer controlled multiple exposures over a range of exposure times and/or aperture settings (f-stops) to provide data for computing an increased dynamic range. The multiple exposures may be made by a 2D sensor of a stationary component, a stationary 1D sensor of a moving component, or a moving 1D sensor of a stationary component. The sensor or component may be advantageously moved by a platform driven by a stepper motor with an encoder on the stepper motor shaft to provide information to the control system 250 as to the motion.

Alternatively, a lensless single-exposure imaging system with a random mask placed in front of an image sensor is utilized such that very point within the field-of-view projects a unique pseudorandom pattern of caustics on the sensor. The pattern of caustics data may then be computationally converted into high-dynamic-range and/or multispectral images.

The control system 250 may include at least one processor 252, a memory 254, and an input/output (I/O) subsystem 256. The control system 250 may be embodied as any type of computing device, a workstation, a server, an enterprise computer system, a network of computers, a combination of computers and other electronic devices, or other electronic devices. The processor 252 and the I/O subsystem 256 are communicatively coupled to the memory 254. The memory 254 may be embodied as any type of computer memory device (e.g., various forms of random access or sequential access memory, permanent or transitory). The I/O subsystem 256 may also be communicatively coupled to a number of hardware, firmware, and/or software components, including a data storage device 254, a display 260, and a user interface (UI) subsystem 262. The data storage device 254 may include one or more hard drives or other suitable persistent storage devices. A database 270 may reside at least temporarily in the data storage device 254 and/or other data storage devices (e.g., data storage devices that are "in the cloud" or otherwise connected to the control system 250 by a network).

The control system 250 may also include other hardware, firmware, and/or software components that are configured to perform the functions disclosed herein, including a driver 280 for a camera controller 284, a driver 282 for a filter controller 286, a non-uniformity correction (NUC) and scan graphical user interface (GUI) 290, and an analysis and temperature map graphical user interface (GUI) 292. The control system 250 may include other computing devices (e.g., servers, mobile computing devices, etc.) and computer aided manufacturer (CAM) systems which may be in communication with each other and/or the control system 250 via a communication network to perform one or more of the disclosed functions.

Figure 3:
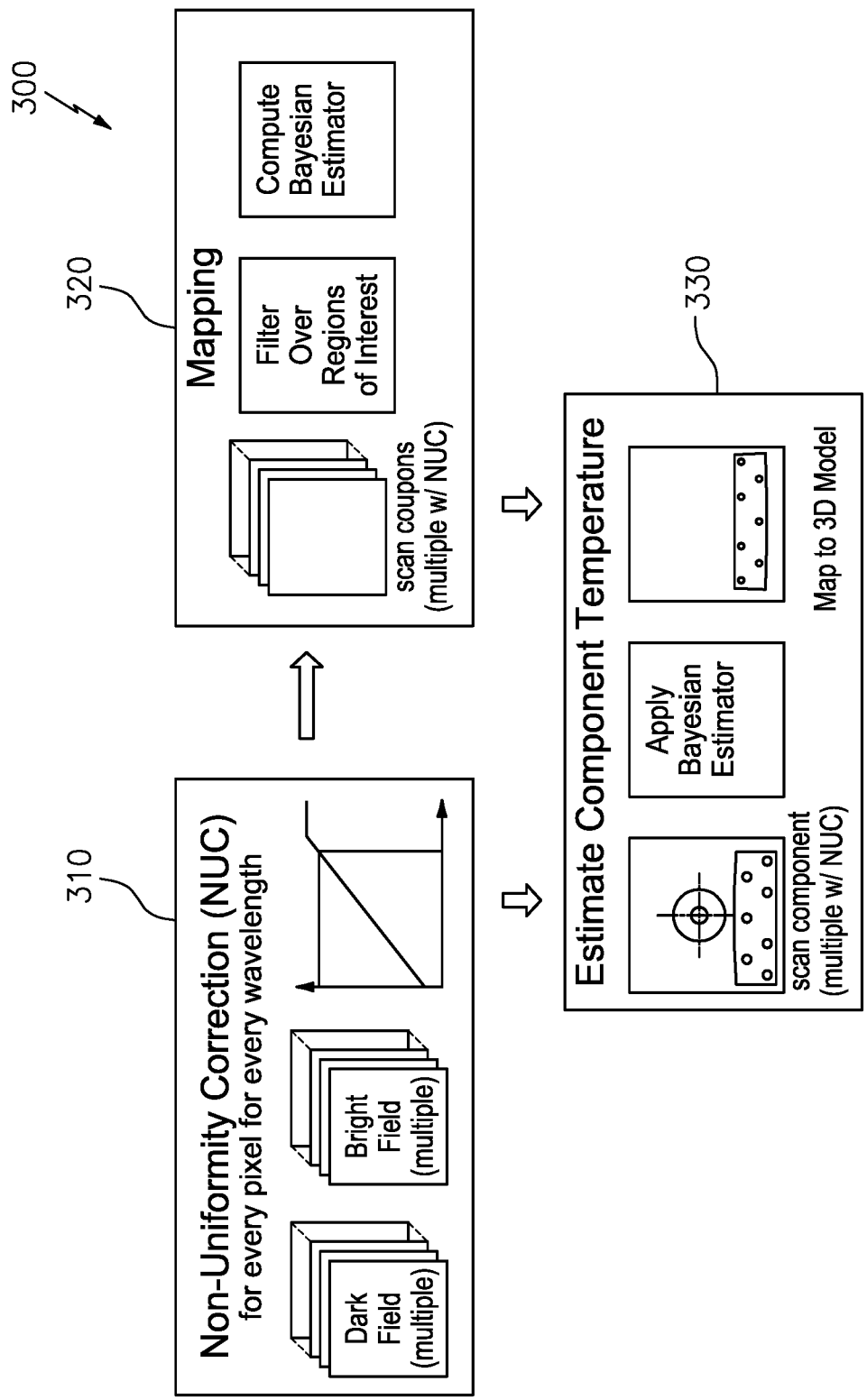
FIG. 3 is a schematic representation of the method of thermally-sensitive coating analysis.
Figure 4:
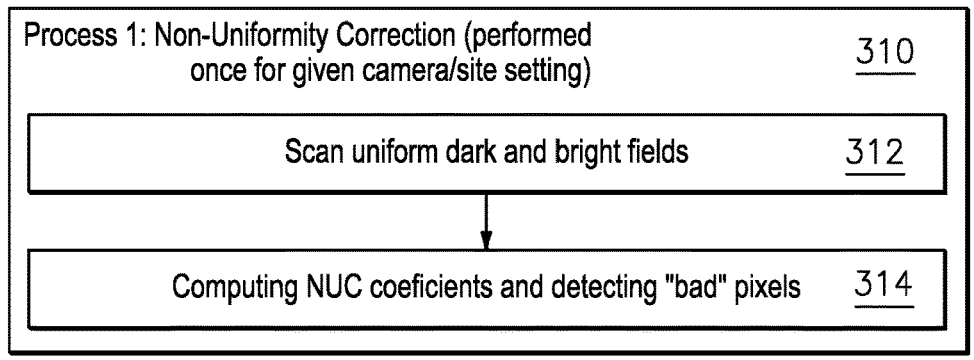
FIG. 4 is a block diagram representing a method of thermally-sensitive coating analysis.
Figure 4:
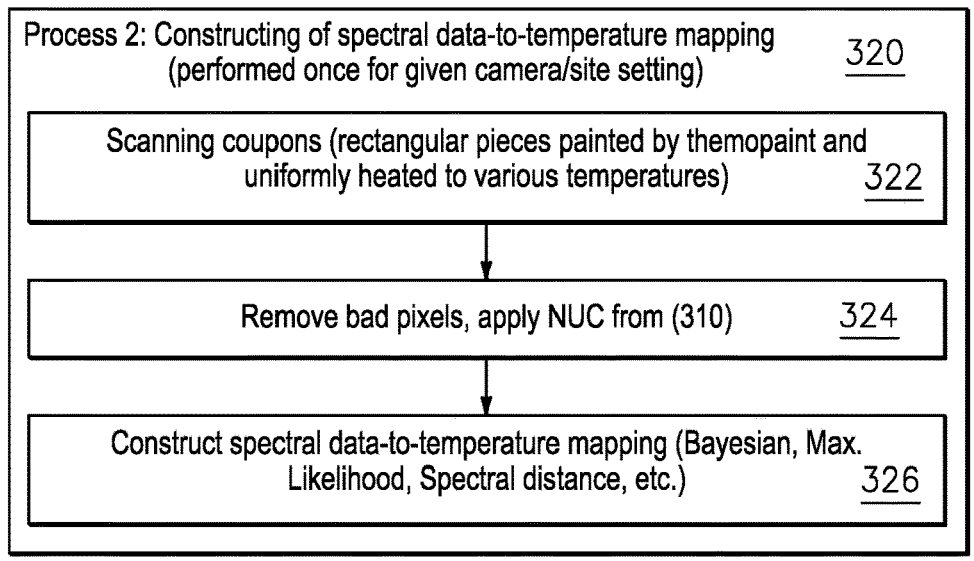
Figure 4:
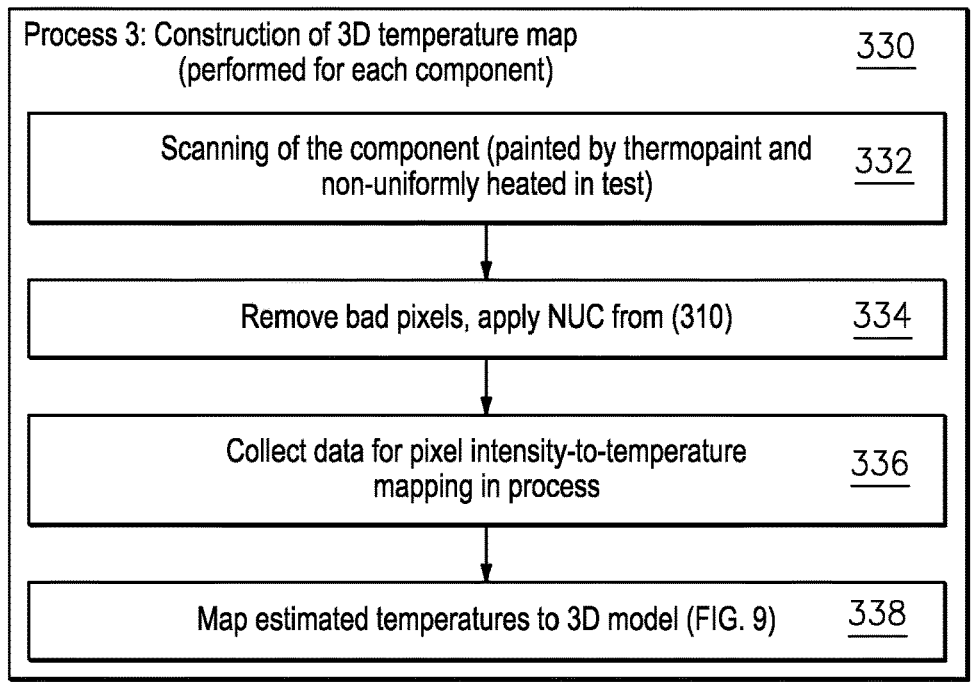

With reference to FIGS. 3 and 4, one disclosed non-limiting embodiment of a method 300 for thermally-sensitive coating analysis includes three primary processes including a non-uniformity correction (NUC) (process 310), mapping (process 320) and component temperature estimation (process 330).

The non-uniformity correction (NUC) process 310 of the method 300, which may be performed once for a given camera/illumination/site setting includes utilizing 3-dimensional arrays in which the data is generated from scans of a "dark field" and scans of a "bright field" (step 312). The thermally-sensitive coating analysis system 200 computes coefficients for the non-uniformity correction (NUC) (step 314) and detects bad pixels to eliminate potentially spurious data or otherwise.

The non-uniformity correction (NUC) may be defined in the form:

$$\text{Corrected intensity} = \text{original intensity} * \text{slope} - \text{shift} \quad (1)$$

where slope and shift are parameters of the transformation. All variables in equation (1) are 3-dimensional fields: (x, y, frequency band), where x and y are the individual pixel coordinates. In this embodiment, two images (or sets of images) are acquired for estimation: a dark field and a bright field, taken at the same conditions (including illumination, exposure time, aperture, and focus). The targets of the camera are backgrounds of two standard intensities). The bright field may be a uniformly reflective surface, sometimes called a gray field or a white field, where the reflectivity does not cause pixel intensities to saturate. In this example, intensities of all pixels of the dark field should be null, and of the bright field should be equal to some fixed number referred to as nominal intensity. The dark field may be a black image (e.g., taken at no light and using a black colored planar background target). In some embodiments, the pixel values of the dark field scan and bright field scan vary such that equation (1) is defined so that corrected intensities of the scans are uniformly equal to 0 and nominal intensity respectively. In alternative non-limiting embodiments, the variables in equation (1) may be a 3-dimensional field (x, y, polarization); a 3-dimensional field (x, y, incident angle); a 4-dimensional field comprising (x, y and any two of frequency band, polarization, and incident angle); a 5 dimensional field (x, y, frequency band, polarization, incident angle); and the like. Incident angle is the angle between the normal vector of the component at a pixel location and the vector to the camera center. In these embodiments the images are acquired over the range(s) of the variable(s). The computation of the NUC, construction of the temperature map, and component temperature mapping are performed analogously to the 3-dimensional (x, y, frequency band) case as described elsewhere herein. When more than one image (scan) is taken of a dark field, bright field, coupon, or component, the scans may be reduced to a single scan by filtering using a mean filter (averaging), a median filter, a rank filter, an adaptive filter, a low-pass filter, inpainting, and the like.

To compute the slope and shift parameters for the (x, y, frequency band) case, the two 3-dimensional arrays, scans of the dark field and scans of the bright field are utilized. The digital signal processing corrects optics and illumination irregularities via repeated scan of the dark field image, the bright field image, and test coupons. At some pixels (x, y, frequency band) the values of the dark field or bright field may be the result of noise or some defect of the optical system. Such pixels are detected and marked as bad pixels. A pixel may be identified as bad if either the value or ratio from dark field value to the bright field value (slope) is greater or less than a threshold. In one example, the dark value threshold may be derived as the mean+3σ of all the dark field values after filtering multiple scans while the bright value threshold may be derived as the mean−3σ of all the bright field values after filtering multiple scans. The ratio threshold may be derived as the mean±3σ of all the slope values after filtering multiple scans. The number of scans may be determined by the convergence of estimates for the mean and standard deviation of pixel values as the number of scans increases. In one non-limiting embodiment, one scan may be sufficient. In other non-limiting embodiments multiple scans may be beneficial to obtain consistent data from ever-changing camera, illumination settings, and electrical noise. The estimates converge when additional scans change the estimate by less than a pre-defined amount, for example about 1%. The scanning may be repeated automatically until convergence is achieved or a predetermined number of iterations have been completed. For all pixels not denoted as bad, a non-uniformity correction (NUC) is computed as in eq. (1). The repeated scans may be filtered, for example, by averaging or with a low pass filter (over space and/or over repeat scans). The data from pixels denoted as bad will not be used in subsequent computation, but may be in-painted, e.g., by deep learning techniques, low-rank approximation, interpolation, and the like.

Figure 5:
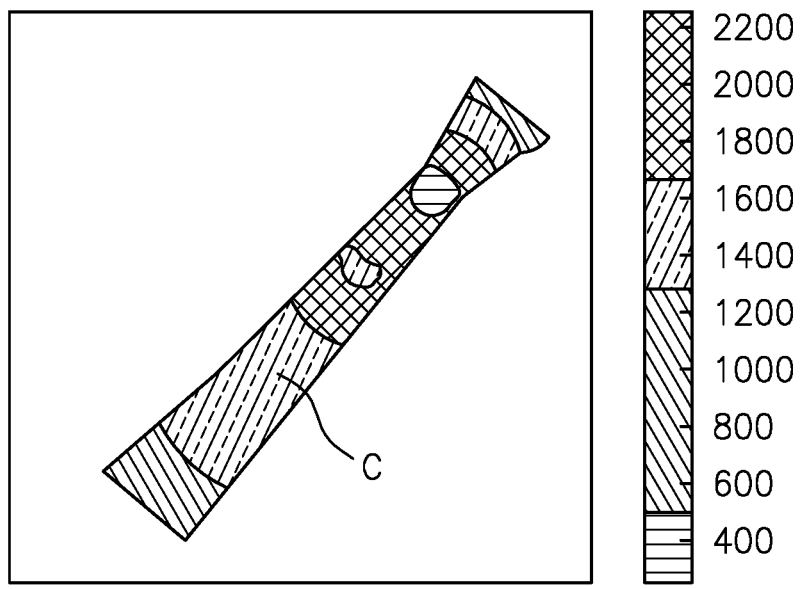
FIG. 5 is a schematic view of a thermally-sensitive coating on a test coupon after exposure to a high temperature.

Next, the constructing of the spectral data-to-temperature mapping 320 of the method 300 is performed. Once the slope and shift parameters are computed, coupons "C" coated with the thermally-sensitive coating 30 and baked at particular known temperatures and durations are scanned (Step 322; FIG. 5). That is, the coupons "C" provide a known reference.

Next, bad pixels are removed (step 324) from coupon scans and the remaining pixel values on a coupon scan are recomputed using the non-uniformity correction (NUC) process 310, accordingly to the formula (1) described elsewhere herein. These pixel values are stored and used for temperature mapping process described elsewhere herein.

The multispectral camera 220 is then utilized to image the thermally-sensitive coated and thermally exposed component 20 (step 332) over a range of substantially distinct frequencies (colors) as filtered by the narrowband multispectral filter 230. The imaging (scans) of component 20 may be performed repeatedly and filtered as described elsewhere herein for other imaging. The imaging may be over frequency, polarization, incident angle, and the like. The 2D image data may be saved to the database 270 for further processing.

Next, bad pixels are removed (step 334) from the component scan (or filtered scan) and the remaining pixel values are recomputed using the non-uniformity correction (NUC) process 310, accordingly to the formula (1) described elsewhere herein.

Next, the 2D temperature map 400 (FIG. 6) is constructed for each component 30 via process 330 by applying data-to-temperature mapping on pixel-by-pixel basis using the data collected in process 320 (step 336). An accurate relationship between temperature, duration, and measured color is thereby identified. In one embodiment, the temperature mapping may be performed by a Spectral Angle Map (SAM). In this method, the coupon data are spatially averaged for each temperature, and sample vectors s(t) are constructed for each temperature t for which a coupon is available. Each component of the vector s(t) is equal to mean (in other possible embodiments—median, weighted mean, or other similar statistics) of pixel intensity of the coupon baked at temperature t, at one spectral band. Similarly, for each pixel x of the component not marked as "bad", intensities at different spectral bands are arranged in the vector d(x) in the same order as in the vectors s(t). Such vectors henceforth will be called spectral vectors. Then temperature t(x) is computed which yields the minimum of $(d^T(x)s(t))/(\|d(x)\|\|s(t)\|)$ over all t. That temperature is accepted as temperature estimate at the location x.

In an alternate embodiment, the temperature mapping may be performed by a Maximal Likelihood method. In this method, coupon data are used to estimate multi-dimensional probability densities $P_t(d)$ for the distribution of spectral vectors for all temperatures t for which coupons are available. In one embodiment the probability density can be estimated using Gaussian families of distributions. Then, for each pixel x of the component, intensities at different spectral bands are arranged in the spectral vector d(x) and the temperature t(x) is computed which yields the maximum $P_t(d(x))$ over all temperatures t.

In yet another embodiment other standard statistical estimation methods such as Bayesian estimation method can be utilized.

After assignment of the temperature to all pixels of a component scan, or filtered component scans, other than bad pixels, the temperature at the locations of bad pixels is assigned by application of a mean filter (averaging), a median filter, a rank filter, an adaptive filter, a low-pass filter, inpainting, and the like) to the temperatures of all the "not bad" pixels in neighborhood of each bad pixel.

The pixel-by-pixel temperature estimation disclosed elsewhere herein may be further improved by methods reflecting the physics of heat conduction. In particular, the temperature of adjacent pixels cannot vary arbitrarily, but must depend on the thermal conductivity of the relevant materials and the component's construction. In one non-limiting embodiment, the temperature map constructed as disclosed elsewhere herein may be improved using Total Variation regularization, by solving the following optimization problem $$minimize_{T(x)} \int \int_x \|T(x) - t(x)\|^2 + \mu \sqrt{\left(\frac{\partial T}{\partial x_1}\right)^2 + \left(\frac{\partial T}{\partial x_2}\right)^2} \, dx$$

where t(x) is the temperature map estimated on a pixel-by-pixel basis by the methods described elsewhere herein, T(x) is updated temperature map, µ is the positive parameter to be chosen on the basis of experiments, individually for each analysis system 200 and/or component 20.

Next, the 3D temperature map is constructed for each component 20 via process 330 of the method 300 is performed. The multispectral camera 220 is then utilized to image the thermally-sensitive coated and thermally exposed component 20 (step 332) over a range of substantially distinct frequencies (colors) as filtered by the narrowband multispectral filter 230. The imaging (scans) of component 20 may be performed repeatedly and filtered as described elsewhere herein for other imaging. The imaging may be over frequency, polarization, incident angle, and the like. The 2D image data may be saved to the database 270 for further processing.

Next, bad pixels are removed (step 334) via the non-uniformity correction (NUC) process 310.

Figure 6:
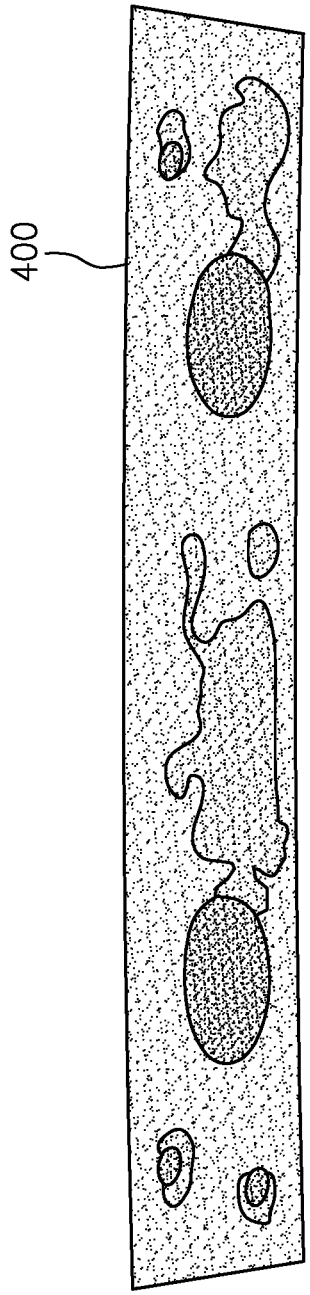
FIG. 6 is a schematic view of a 2D temperature map data of the component.

Next, the spectral data-to-temperature mapping from procedure 320 is applied (step 336) to obtain the 2D temperature map 400 (FIG. 6).

Figure 7:
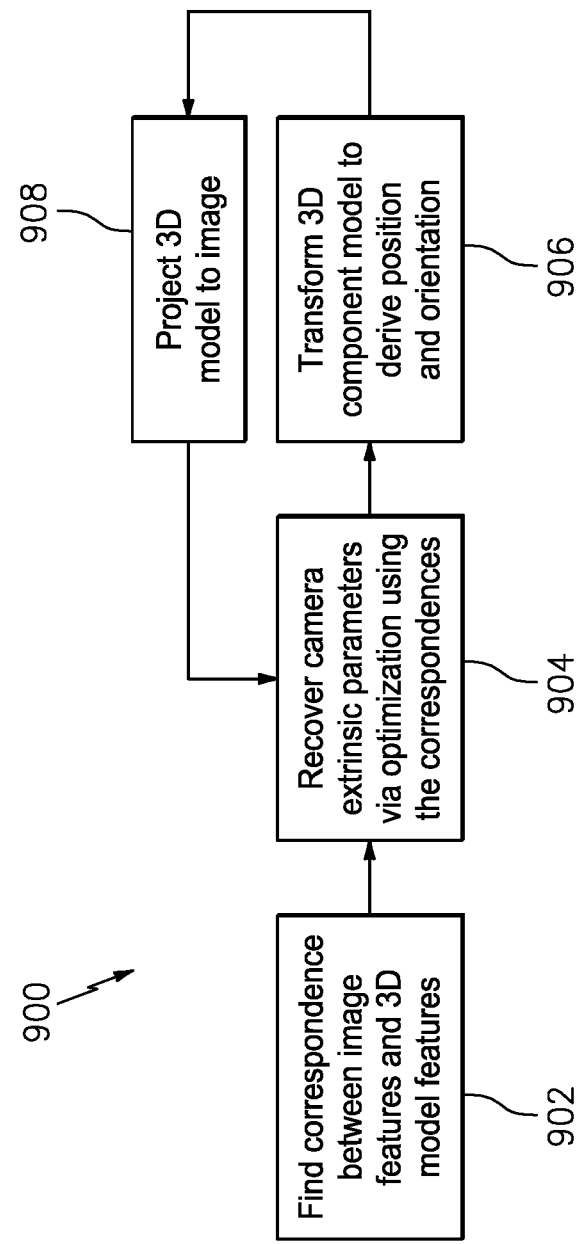
FIG. 7 is a block diagram representing projecting the 2D temperature map data to a 3D CAD model of the component.
Figure 8:
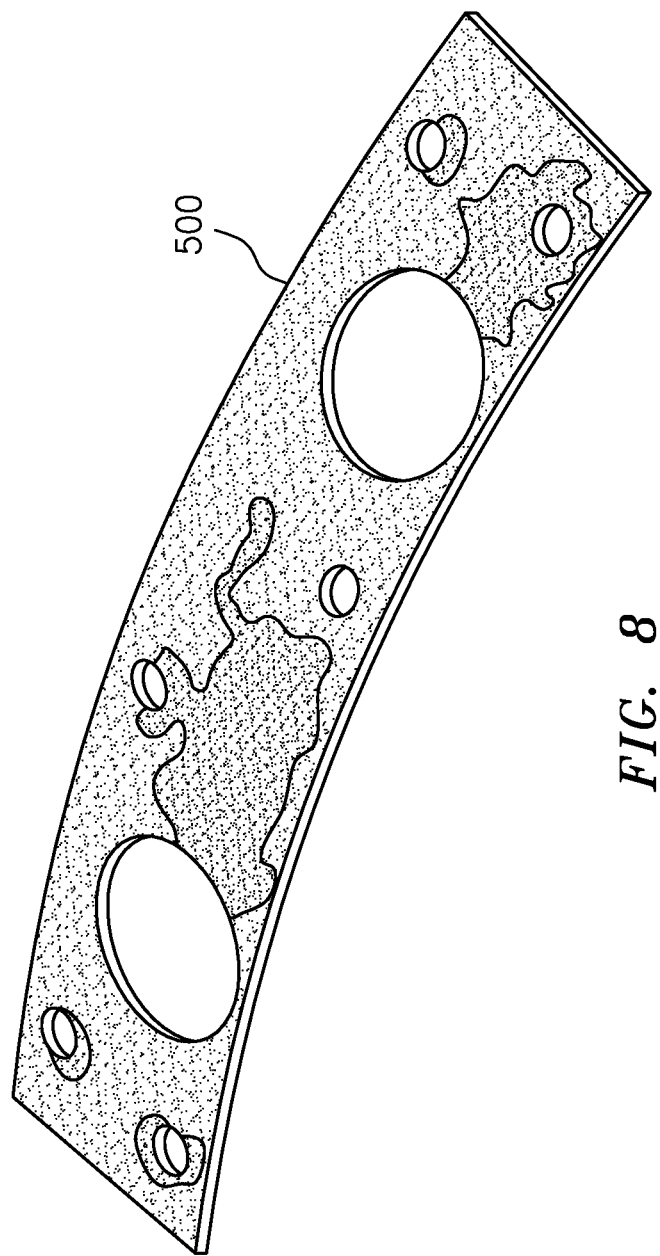
FIG. 8 is a schematic view of a 3D CAD model of the component with a superimposed temperature map.

Next, the 2D temperature map 400 data is mapped to a 3D CAD model 500 (FIG. 8) of the component 20 (step 338; process 900 FIG. 7). The mapping may be performed via the definition of a cost function that minimizes errors between the 3D coordinates by back-projecting features from 2D temperature map 400. The 2D image is projected and mapped onto the 3D model using geometric and computer vision methods (process 900). This process can proceed iteratively to improve accuracy. Areas on the component that do not have a thermally sensitive coating, such as holes, along edges or out of line-of-sight, can be detected and automatically removed from the mapping process by 2D image analytics.

The mapping of the 2D temperature map 400 to the 3D CAD model 500 may be performed by deriving a transformation that transforms the 3D CAD model 500 vertices to 2D pixel coordinates. For example, the transformation can be formulated as a 3×4 matrix containing 11 independent parameters when 2D image pixels and 3D model vertices are represented in homogeneous coordinates. These parameters define relative translation, rotation, stretching, squeezing, shearing, and a 3D-to-2D projection. A minimum of 6 pairs of 3D vertices and 2D pixel coordinates are identified to be corresponding to each other from the image and the 3D model. The identification can be either manual, semi-automatic, or fully automatic. The coordinates of these pixels and vertices can be used first to solve a linear regression problem to get an initial estimate of the 11 parameters. This initial estimate can then be used as starting point to solve a non-linear regression problem using an algorithm such as Gauss-Newton or Levenberg-Marquardt. As a result, the refined values of the 11 parameters can be used to transform the 3D CAD model 500 to match closely with 2D pixels. The 3D CAD model 500 vertices can obtain temperature values from those of their projected coordinates. This mapping uses forward projection, by projecting 3D CAD model 500 vertices to 2D temperature image coordinates.

The mapping of the 2D temperature map 400 to the 3D CAD model 500 may be performed, in another embodiment, using backward projection. First the 3D vertices are triangulated to form 3D planar triangular surfaces. Then camera center coordinates are calculated from the transformation matrix. Next every image pixel is back-projected though finding an intersection between the line connecting the pixel and the camera center with a 3D planar triangular surface patch. In this way, not only the 3D model vertices obtain temperature values, but also the triangular surface patches, increasing the resolution of the 3D model in terms of temperature mapping. The mapping of the 2D temperature map 400 to the 3D CAD model 500 may be performed, in yet another embodiment, by combining the above two methods.

In another embodiment, a Bayesian color-to-temperature method may be utilized. Here, the parameters of the distribution of color intensity versus temperature and wavelength are determined from calibration coupons. The conditional distributions of intensity given temperature are known for all wavelengths and assumed independent. Bayes' theorem is used to update the posterior probability of temperature given intensity in the image on a pixel-by-pixel basis.

With reference to FIG. 7, one embodiment of a method 900 of mapping the 2D temperature map of component 20 to a 3D CAD model 500 of the component 20 initially includes finding a correspondence between a feature of the 2D temperature map and a feature of the 3D model (step 902) for all available 2D/3D feature pairs. The correspondence may be found by a random sample consensus (RANSAC) algorithm. Next, the extrinsic parameters of high-resolution high-dynamic-range camera 220 are recovered via optimization using the correspondences (step 904). Next, the 3D model is transformed according to the derived extrinsic parameters including position and orientation (step 906) then the 2D temperature map is projected (step 908) with respect to the extrinsic parameters. The optimization then repeats. After the optimization process converges, vertices of the 3D model are projected to the 2D temperature map to get their temperatures. In another embodiment, temperature values of the pixels on the 2D temperature map can also be back-projected to the 3D model to assign vertices of the 3D model temperature values.

The method 300 corrects many of the deficiencies and inaccuracies of existing thermally-sensitive coating image processing techniques by using information about features of the actual scanned component, in the form of a computer model, as well as enhancing the accuracy of the temperature measurements and the estimation process. The automated multispectral inspection system provides detection and quantification of temperature exposure or time-temperature exposure and the automated mapping of that exposure to a 3D CAD model 500 of the component. The method 300 provides a signal to noise improvement by automatically taking multiple scans of the component; a dynamic range improvement from both the camera hardware and signal processing; an accuracy improvement by use of an optimal estimator, and an accuracy and convenience improvement of automated mapping to a 3D CAD model 500 using image analytics.

The use of the terms "a", "an", "the", and similar references in the context of description (especially in the context of the following claims) are to be construed to cover both the singular and the plural, unless otherwise indicated herein or specifically contradicted by context. The modifier "about" used in connection with a quantity is inclusive of the stated value and has the meaning dictated by the context (e.g., it includes the degree of error associated with measurement of the particular quantity). All ranges disclosed herein are inclusive of the endpoints, and the endpoints are independently combinable with each other. It should be appreciated that relative positional terms such as "forward", "aft", "upper", "lower", "above", "below", and the like are with reference to normal operational attitude and should not be considered otherwise limiting.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be appreciated that like reference numerals identify corresponding or similar elements throughout the several drawings. It should also be appreciated that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason, the appended claims should be studied to determine true scope and content.

What is claimed is:

1. A method for non-destructive thermally-sensitive coating analysis of a component under inspection, the method comprising:
   performing one or more scans of a thermally-sensitive coated and thermally exposed component to generate image data via a multispectral camera displaced from the component;
   estimating parameters of non-uniformity correction (NUC) for one or more pixels of one or more dark field images and one or more corresponding pixels of one or more bright field images;
   constructing a 2D temperature map for one or more pixels of the scanned image using the parameters from the non-uniformity correction; and
   mapping the 2D temperature map to a 3D computer aided design (CAD) model of the component using image analytics in which repeated scans continue automatically until one or more of a convergence and a fixed number of iterations is reached, wherein the repeated scans comprise one or more repeated scans of a dark field image, a bright field image, a test coupon, and the component, the mapping of each of the repeated scans comprises:
   finding a correspondence between a feature of the 2D temperature map and a feature of the 3D model;
   recovering extrinsic parameters via optimization using the correspondence;
   transforming the 2D temperature map to derive positioning and orientation; and
   projecting the 2D temperature map with respect to the extrinsic parameters.

2. The method as recited in claim 1, wherein the scanning is over one or more of a range of distinct frequencies as selected by a narrowband variable filter, a distinct range of polarizations, and a distinct range of incident angles.

3. The method as recited in claim 1, wherein mapping the 2D temperature map to a 3D computer aided design (CAD) model comprises defining a cost function and minimizing the error between the 3D coordinates by back-projecting features from the 2D temperature map.

4. The method as recited in claim 3, wherein the mapping comprises using a non-linear least squares method.

5. The method as recited in claim 1, wherein estimating parameters of non-uniformity correction (NUC) comprises defining intensities of one or more pixels of the dark field as null and defining intensities of corresponding one or more pixels of the bright field to a nominal intensity.

6. The method as recited in claim 1, wherein estimating parameters of non-uniformity correction (NUC) comprises detecting bad pixels.

7. The method as recited in claim 6, wherein detecting bad pixels comprises determining if a value or difference from the dark value to the bright value (slope) is greater than a threshold.

8. The method as recited in claim 7, wherein detecting bad pixels comprises determining if a ratio from the bright value to the dark value (slope) is greater than a threshold.

9. The method as recited in claim 8, wherein the dark value threshold is derived as being the mean+3σ of all the dark field values.

10. The method as recited in claim 8, wherein the bright value threshold is derived as being the mean−3σ of all the bright field values.

11. The method of claim 1, wherein one or more of the scans, dark field images, and bright field images are filtered by one or more of a mean filter (averaging), a median filter, a rank filter, an adaptive filter, a low-pass filter, and inpainting.

12. The method as recited in claim 11, wherein one or more of the dark value threshold is derived as being the mean+3σ of all the filtered dark field values, and the bright value threshold is derived as being the mean−3σ of all the filtered bright field values.

13. The method as recited in claim 1, wherein one or more of a number of scans, number of dark field images, and number of bright field images is determined by the convergence of estimates for one or more of a mean and a standard deviation as the number of scans increases.

14. The method as recited in claim 13, wherein the estimates converge when additional scans change the estimate by less than a pre-defined amount.

15. The method as recited in claim 14, wherein the pre-defined amount is 1%.

16. The method as recited in claim 1, wherein at least the dark field image and the bright field image are taken at the same conditions.

17. The method as recited in claim 1, wherein intensities of all pixels of the dark field image are null, and the bright field is equal to a fixed number referred to as nominal intensity.

18. The method as recited in claim 1, wherein the bright field image is a uniformly reflective surface.

19. A non-destructive thermally-sensitive coating analysis system comprising:
   a multispectral camera;
   one or more of a narrowband multispectral filter, a polarization filter, an incident angle variation for the multispectral camera displaced from the component under inspection; and
   a control system operable to map a 2D temperature map from the multispectral camera to a 3D CAD model of the component using image analytics in which repeated scans by the multispectral camera are filtered, wherein the repeated scans continue automatically until one or more of a convergence and a fixed number of iterations is reached, the repeated scans comprise one or more repeated scans of a dark field image, a bright field image, a test coupon, and the component.

20. The system as recited in claim 19, wherein the filtering comprises one or more of a mean filter (averaging), a median filter, a rank filter, an adaptive filter, a low-pass filter, and inpainting.

\* \* \* \* \*